(12) United States Patent
Buchanan

(10) Patent No.: US 10,099,061 B2
(45) Date of Patent: Oct. 16, 2018

(54) EMERGENCY APPARATUS INDICATOR

(71) Applicant: Physio-Control, Inc., Redmond, WA (US)

(72) Inventor: Robert Reuben Buchanan, Bothell, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

(21) Appl. No.: 14/553,994

(22) Filed: Nov. 25, 2014

(65) Prior Publication Data

US 2016/0148495 A1   May 26, 2016

(51) Int. Cl.
*A61N 1/39* (2006.01)

(52) U.S. Cl.
CPC .............. *A61N 1/39* (2013.01); *A61N 1/3993* (2013.01)

(58) Field of Classification Search
CPC ...... A61B 5/0002; G06Q 10/08; G08B 25/10; G08B 25/016
USPC ............. 340/539.17, 539.18, 539.13, 539.12
See application file for complete search history.

(56) References Cited

U.S. PATENT DOCUMENTS

| | | | | |
|---|---|---|---|---|
| 6,292,687 | B1* | 9/2001 | Lowell | A61B 5/1112 600/515 |
| 8,565,871 | B2* | 10/2013 | Tuysserkani | A61B 5/0022 340/539.12 |
| 8,930,044 | B1* | 1/2015 | Peeters | B64C 19/00 701/2 |
| 9,026,147 | B2* | 5/2015 | Galvin | G01S 19/17 455/456.1 |
| 9,067,080 | B2* | 6/2015 | Einy | A61N 1/39 |
| 2004/0124979 | A1* | 7/2004 | Medema | A61N 1/39 340/539.18 |
| 2006/0149323 | A1* | 7/2006 | Merry | A61N 1/39 607/5 |
| 2009/0201147 | A1* | 8/2009 | Gottlieb | G08B 25/016 340/539.12 |
| 2009/0315735 | A1* | 12/2009 | Bhavani | G06Q 10/06 340/8.1 |
| 2011/0117878 | A1* | 5/2011 | Barash | H04W 4/90 455/404.2 |
| 2013/0338724 | A1* | 12/2013 | Joo | A61N 1/3987 607/3 |
| 2014/0085082 | A1* | 3/2014 | Lyon | A61B 5/746 340/539.12 |
| 2014/0159893 | A1* | 6/2014 | Housley | G08B 21/0269 340/539.13 |
| 2014/0266736 | A1* | 9/2014 | Cretu-Petra | A61F 13/42 340/573.5 |
| 2015/0094604 | A1* | 4/2015 | Amann | A61B 5/04325 600/510 |
| 2015/0186601 | A1* | 7/2015 | Waxman | G06F 19/322 705/3 |

* cited by examiner

*Primary Examiner* — Firmin Backer
*Assistant Examiner* — Munear Akki
(74) *Attorney, Agent, or Firm* — Lane Powell PC

(57) ABSTRACT

Technologies and implementations for configuring of automated emergency medical equipment beacon are generally disclosed. The emergency medical equipment may provide a beacon indicating location and event of the emergency.

17 Claims, 12 Drawing Sheets

900 A computer program product

902 A signal bearing medium 904 at least one of machine readable non-transitory medium having stored therein instructions that, when executed by one or more processors, operatively enable a defibrillator electrode having communicative capabilities to:

receive, via an electronic communication medium, an indication of a need for an emergency apparatus, the indication including information regarding a location of the need;

determine if the location of the need is within a predetermined radius relative to a location of the emergency apparatus, the determination based, at least in part, on the information regarding the location of the need; and if it is determined that the location of the need is within the predetermined radius, activate an electronic indicator device.

| 906 a computer-readable medium | 908 a recordable medium | 910 a communications medium |

Figure 9

1000 A computer program product

1002 A signal bearing medium 1004 at least one of machine readable non-transitory medium having stored therein instructions that, when executed by one or more processors, operatively enable a defibrillator electrode having communicative capabilities to:

receive at an emergency apparatus, via an electronic communication medium, an indication of a need for the emergency apparatus, the indication including information regarding a location of the need;

determine if the location of the need is within a predetermined radius relative to a location of the emergency apparatus, the determination based, at least in part, on the information regarding the location of the need;

determine if the emergency apparatus is operationally ready for use; and if it is determined that the location of the need is within the predetermined radius and that the emergency apparatus is operationally ready for use, activate an electronic indicator device.

| 1006 a computer-readable medium | 1008 a recordable medium | 1010 a communications medium |

Figure 10

1100 A computer program product

1102 A signal bearing medium 1104 at least one of machine readable non-transitory medium having stored therein instructions that, when executed by one or more processors, operatively enable a defibrillator electrode having communicative capabilities to:

receive at an emergency apparatus, via an electronic communication medium, an indication of a need for the emergency apparatus, the indication including information regarding a location of the need;

determine if the location of the need is within a predetermined radius relative to a location of the emergency apparatus, the determination based, at least in part, on the information regarding the location of the need;

determine if motion is detected proximate to the emergency apparatus; and if it is determined that the location of the need is within the predetermined radius and/or that motion is detected, activate an electronic indicator device.

| 1106 a computer-readable medium | 1108 a recordable medium | 1110 a communications medium |

Figure 11

EMERGENCY APPARATUS INDICATOR

BACKGROUND

Unless otherwise indicated herein, the approaches described in this section are not prior art to the claims in this application and are not admitted to be prior art by inclusion in this section.

When there is a medical emergency, locating an emergency apparatus that may provide assistance to the medical emergency may be important. For example, an emergency apparatus such as, but not limited to, an automated external defibrillator (AED) have become more prevalent in various public/private areas. It may be appreciated that AEDs may be found in airports, subway stations, office buildings, outdoors areas, etc. Accordingly, if a person is experiencing a medical event, where an AED may provide assistance, locating an AED or AEDs may be important to get the AED to the person as fast as possible.

SUMMARY

The present disclosure describes example methods, apparatus, and systems related to facilitating indication of a location of an emergency apparatus. An example method may include a method of facilitating indication of an emergency apparatus, where the method may include receiving, via an electronic communication medium, an indication of a need for an emergency apparatus, the indication including information regarding a location of the need, determining if the location of the need is within a predetermined radius relative to a location of the emergency apparatus, the determining based, at least in part, on the information regarding the location of the need, and if it is determined that the location of the need is within the predetermined radius, activating an electronic indicator device.

Another example method may include a method of facilitating indication of an emergency apparatus, where the method may include receiving at the emergency apparatus, via an electronic communication medium, an indication of a need for the emergency apparatus, the indication including information regarding a location of the need, determining if the location of the need is within a predetermined radius relative to a location of the emergency apparatus, the determining based, at least in part, on the information regarding the location of the need, determining if the emergency apparatus is operationally ready for use, and if it is determined that the location of the need is within the predetermined radius and that the emergency apparatus is operationally ready for use, activating an electronic indicator device.

Another example method may include a method of facilitating indication of an emergency apparatus, where the method may include receiving at the emergency apparatus, via an electronic communication medium, an indication of a need for the emergency apparatus, the indication including information regarding a location of the need, determining if the location of the need is within a predetermined radius relative to a location of the emergency apparatus, the determining based, at least in part, on the information regarding the location of the need, determining if motion is detected proximate to the emergency apparatus, and if it is determined that the location of the need is within the predetermined radius and/or that motion is detected, activating an electronic indicator device.

The present disclosure also describes various example machine readable media having stored therein instructions that, when executed by one or more processors, operatively enable an indication alert module to receive, via an electronic communication medium, an indication of a need for an emergency apparatus, the indication including information regarding a location of the need, determine if the location of the need is within a predetermined radius relative to a location of the emergency apparatus, the determination based, at least in part, on the information regarding the location of the need, and if it is determined that the location of the need is within the predetermined radius, activate an electronic indicator device.

The present disclosure also describes various example machine readable media having stored therein instructions that, when executed by one or more processors, operatively enable an indication alert module to receive at an emergency apparatus, via an electronic communication medium, an indication of a need for the emergency apparatus, the indication information regarding a location of the need, determine if the location of the need is within a predetermined radius relative to a location of the emergency apparatus, the determination based, at least in part, on the information regarding the location of the need, determine if the emergency apparatus is operationally ready for use, and if it is determined that the location of the need is within the predetermined radius and that the emergency apparatus is operationally ready for use, activate an electronic indicator device.

The present disclosure also describes various example machine readable media having stored therein instructions that, when executed by one or more processors, operatively enable an indication alert module to receive at an emergency apparatus, via an electronic communication medium, an indication of a need for the emergency apparatus, the indication including information regarding a location of the need, determine if the location of the need is within a predetermined radius relative to a location of the emergency apparatus, the determination based, at least in part, on the information regarding the location of the need, determine if motion is detected proximate to the emergency apparatus, and if it is determined that the location of the need is within the predetermined radius and/or that motion is detected, activate an electronic indicator device.

The present disclosure additionally describes example systems for facilitating indication of an emergency apparatus. Example systems may include a transmit and/or receive module (TX/RX), a processor communicatively coupled to the TX/RX, and a indication alert module (IAM) communicatively coupled to the processor, the IAM configured to receive, via an electronic communication medium, an indication of a need for an emergency apparatus, the indication including information regarding a location of the need, determine if the location of the need is within a predetermined radius relative to a location of the emergency apparatus, the determination based, at least in part, on the information regarding the location of the need, and if it is determined that the location of the need is within the predetermined radius, activate an electronic indicator device.

Another example system may include a transmit and/or receive module (TX/RX), a processor communicatively coupled to the TX/RX, and a indication alert module (IAM) communicatively coupled to the processor, the IAM configured to receive at an emergency apparatus, via an electronic communication medium, an indication of a need for the emergency apparatus, the indication including information regarding a location of the need, determine if the location of the need is within a predetermined radius relative to a location of the emergency apparatus, the determination based, at least in part, on the information regarding the location of the need, determine if the emergency apparatus is operationally ready for use, and if it is determined that the location of the need is within the predetermined radius and that the emergency apparatus is operationally ready for use, activate an electronic indicator device.

In yet another example system may include a transmit and/or receive module (TX/RX), a processor communicatively coupled to the TX/RX, and a indication alert module (IAM) communicatively coupled to the processor, the IAM configured to receive at an emergency apparatus, via an electronic communication medium, an indication of a need for the emergency apparatus, the indication including information regarding a location of the need, determine if the location of the need is within a predetermined radius relative to a location of the emergency apparatus, the determination based, at least in part, on the information regarding the location of the need, determine if motion is detected proximate to the emergency apparatus, and if it is determined that the location of the need is within the predetermined radius and/or that motion is detected, activate an electronic indicator device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings:

FIG. 9 illustrates an example computer program product 900, arranged in accordance with at least some embodiments;

FIG. 10 illustrates an example computer program product 1000, arranged in accordance with at least some embodiments;

FIG. 11 illustrates an example computer program product 1100, arranged in accordance with at least some embodiments.

DETAILED DESCRIPTION

Figure 1:
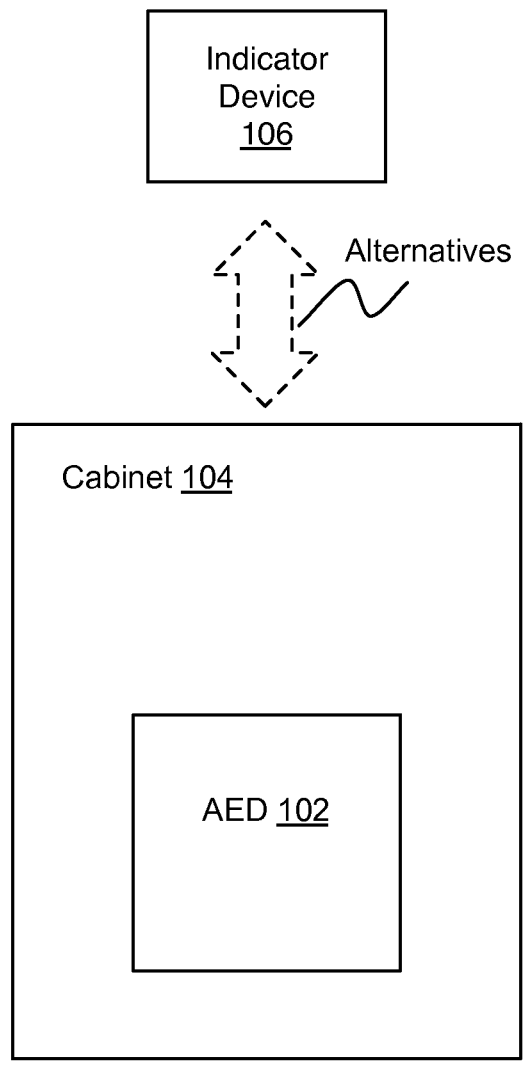
FIG. 1 illustrates a system for facilitating location information of emergency apparatus, in accordance with various embodiments.

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, and systems related to an electronic apparatus capable of facilitating an indication of a location of the emergency apparatus. Such an emergency apparatus may include an electronic medical device. An example electronic medical device may include a user interface to facilitate display of location information of the electronic medical device itself and/or facilitate display of location information of another electronic device nearby. Additionally, such an electronic medical device may include visual and/or audio indicators, which may act as a beacon to help facilitate making its location known.

Commonly, emergency situations may involve an emergency apparatus to help address the emergency situation. For example, medical related issues may involve electronic medical devices to facilitate treatment.

Continuing with the non-limiting example of the medical related issues, heart related issues have become prevalent throughout many parts of the World. For example, in the United States, coronary heart disease may be considered a growing health problem. Coronary heart disease may lead to issues related to the heart such as, but not limited to, arrhythmia. Some arrhythmias may lead to a condition known as sudden cardiac arrest (SCA). An example condition of SCA may be ventricular fibrillation (VF), where the heart muscles may basically quiver and not pump blood. Such conditions may be detected, monitored, and treated utilizing electronic devices.

In order to treat a heart in a condition of VF, the heart may need to be defibrillated by the application of an electrical signal (e.g., an electric shock). In order to defibrillate the heart, an electronic medical device such as a defibrillator device may be utilized. A defibrillator device may facilitate administration of an electrical shock to the heart, thereby defibrillating the heart undergoing VF. The shock may terminate VF providing the heart the opportunity to resume pumping blood. If VF is not terminated, the shock may be repeated at varying energies or VF may eventually lead to the death of the person.

A challenge with defibrillation may be that the electrical shock should be administered very soon after the onset of VF. In order to facilitate administration of electrical shock soon after the onset of VF, alerting emergency personnel and/or bystanders of the need for treatment of VF may be necessary. There may be a variety of ways to alert emergency personnel and/or bystanders. One example may be that a person may be wearing a wearable electronic device, which may facilitate monitoring of the person's heart. If the wearable electronic device detects the onset of VF, the wearable electronic device may be capable of transmitting an electronic signal to alert emergency personnel and/or bystanders. Another example may include a portable electronic device, such as, but not limited to a smart phone. At the onset of VF, a person may activate an application on the smart phone to transmit an electronic signal to alert emergency personnel and/or bystanders. In yet another example, a person may have a wireless transmitter that may be configured to be activated during an emergency. It should be appreciated that the person undergoing VF should receive treatment including defibrillation as quickly as possible.

An electronic medical device, such as, but not limited to an external type of defibrillator device may be utilized to defibrillate the heart. There may be several types of external defibrillator devices such as, but not limited to, wearable defibrillators, manual defibrillators, semi-automated defibrillators, and automated defibrillators. An example type of external defibrillator device may include defibrillator devices intended to treat multiple people such as, but not limited to defibrillators devices that may be found in medical centers and may be described as advanced life support (ALS) type defibrillator devices. ALS type defibrillator devices may have a wide range of functionalities including allowing healthcare professionals to monitor a person's rhythm and manually intervene if is determined that a shock is necessary.

Another example type of external defibrillator device may include a defibrillator device intended to treat a limited number of people such as, but not limited to, a single person. Single person type external defibrillators may include relatively small (i.e., portable) external defibrillator devices. An example of a single person type external defibrillator may be an automated external defibrillator (AED) type device. AED type devices may be found in various private and/or public places such as, but not limited to, offices, train stations, airports, stadiums, hospitals, homes, vehicles, vessels, planes, trains, automobile, etc. AED type devices may be commonly for use by a layperson and/or a person with basic life support training.

For the purposes of describing the disclosed subject matter, references may be made to AED type devices. However, it should be appreciated that AED type devices are but one non-limiting example, and accordingly, in this respect, the claimed subject matter is not limited.

Continuing with the non-limiting example of an AED type device, one or more AEDs may be located in a wide variety of locations. However, location information of the AEDs may not be readily available for a potential user of the AED to provide assistance to the person undergoing VF. For example, there may be several AEDs located in proximity to a person undergoing VF, but locating the closest AED or AEDs to the person undergoing VF by a potential rescuer may be difficult. Even though various methodologies may provide location information of AEDs within an area (e.g., PulsePoint app available from PulsePoint Foundation of Pleasanton, Calif.), actually locating the AEDs themselves may be difficult. As part of a non-limiting example, usage of an AED may be described in accordance with various embodiments of the present disclosure.

In an example scenario, a person may be in a public area. For this example, the public area may be an outdoor park. The person may experience an onset of a medical related event such as, but not limited to, VF/a person in need (here on out PIN). The PIN themselves or a person nearby may have the capabilities of transmitting an indication of the medical related event to facilitate a request for assistance. An example may be a wearable device, which may be capable of monitoring the person's health and be capable of transmitting the indication of the medical related event to an emergency service system (e.g., PulsePoint). Another example may be the person and/or a person witnessing the medical related event contacting an emergency service system such as, but not limited to, 911.

In one example scenario, an emergency apparatus indicator device may receive the indication of the medical related event. Responsive to the received indication, the emergency apparatus indicator device may activate an audio and/or visual indicator that may alert people nearby (e.g., potential rescuer) that a PIN is in need of assistance, and in particular, in need of an emergency apparatus. The emergency apparatus indicator device may facilitate indication of an emergency apparatus, which may be associated with an emergency apparatus close by.

In another example scenario, an emergency apparatus such as, but not limited to, an electronic medical device in the form of an AED may receive the indication of the medical related event. Responsive to the received indication, the AED may activate an audio and/or visual indicator that may alert people nearby (e.g., potential rescuer) that a PIN is in need of assistance, and in particular, in need of an AED. That is, the AED may be capable of indicating, "Here I am and I am needed". For example, a cabinet holding the AED may have a flashing light on top of the cabinet. Alternatively or additionally, the cabinet holding the AED may have a speaker to emit a siren of some kind.

In addition to the capabilities of activation of the indication, an emergency apparatus (e.g., AED) may be coupled with a self propelled vehicle such as, but not limited to, unmanned aerial vehicle (UAV). The UAV may be capable of transporting the AED from its resting place to the location of the PIN. An example of a UAV may be a UAV, such as, but not limited to a UAV available from Amazon.com, Inc. of Seattle, Wash., aka "Octocopter", which may be capable of transporting an AED to the location of the PIN. In this example, an indicator may be included with the AED thereby the indicator may travel with the AED. Alternatively, the indicator may be included with the UAV providing a signal while traveling with the AED. Another alternative example may include more than one indicator, one at the resting place of the AED and another on the AED itself. Accordingly, the claimed subject matter is not limited in these respects.

The potential rescuer may notice the audio and/or visual indicator, and knowing that the audio and/or visual indicator indicates that a PIN is in need of an emergency apparatus, the potential rescuer may obtain the emergency apparatus (e.g., AED) (i.e., may open the AED holding cabinet and retrieve the AED). In order to aid the potential rescuer in locating the PIN, the AED may include a display device, which may have mapping capabilities, showing the location of the PIN relative to the location of the AED. The potential rescuer may retrieve the AED and proceed to follow the map on the display to find and use the AED on the PIN. It may be appreciated that because providing assistance may be urgent, AEDs within a certain proximity to the PIN may respond. Mapping capabilities may include mapping information such as, but not limited to, static mapping information, interactive mapping, voice recognition information (e.g., recognizing such audio information as "corner of $12^{th}$ and Yamhill), global positioning system (GPS) information, and so forth.

Turning now to the figures, FIG. 1 illustrates a system for facilitating location information of emergency apparatus, in accordance with various embodiments. In FIG. 1, system 100 may include an emergency apparatus (e.g., an AED 102) and a cabinet 104. The cabinet 104 may be configured to hold the AED 102. Additionally, system 100 may include an indicator device 106. The AED 102 and the indicator device 106 may be proximate to each other, whereby the indicator device 106 may activate facilitating an indication of a location of the AED 102, in accordance with various embodiments.

In one example, in systems 100, the indicator device 106 may receive a signal indicating that a person is in need of an AED (PIN). Responsive to the received indication, the indicator device 106 may activate. The indication may be in a wide variety of manners. For example, the indication may be in the form of a visual indication (e.g., light, strobe, etc.). Alternatively or in addition to, the indication may be in the form of an audio indication (e.g., siren, loudspeaker, etc.) or any combination thereof.

The indicator device 106 may include a wide variety of indicator devices such as, but not limited to, lights capable of flashing, rotating and/or oscillating lights, strobe lights, an electronic display, an electronic projection, a siren, a loudspeaker, a bell, a vibrating device, etc., and any combination thereof. Accordingly, the claimed subject matter is not limited in scope in these respects.

In another example, in the system 100, the AED 102 may receive a signal indicating that a person is in need of an AED (PIN). Responsive to the received indication, the AED 102 may transmit a signal to the indicator device 106 to activate the indicator device 106. Upon receipt of the signal from the AED 102, the indicator device 106 may activate some form of indication. The indication may be in a wide variety of manners. As described, the indication may be in the form of a visual indication (e.g., light, strobe, etc.). Alternatively or in addition to, the indication may be in the form of an audio indication (e.g., siren, loudspeaker, etc.) or any combination thereof.

In some examples, the AED 102 may be communicatively coupled to the indicator device 106. The AED 102 may be communicative coupled to the indicator device 106 by utilizing a wide variety of communicative capabilities, and accordingly, as part of the communicative capabilities, it is contemplated within the scope of the claimed subject matter that the communicative capabilities may include a wide variety of communicative capabilities such as, but not limited to, wired, wireless, infrared communication, near field communication (NFC), Bluetooth, Wi-Fi (any implementation of wireless protocols, e.g., 802.11 and its variations), and/or any combination thereof. Accordingly, the claimed subject matter is not limited in scope to the particular implementations described herein.

As previously described, the indicator device 106 may include a wide variety of indicator devices such as, but not limited to, lights capable of flashing, rotating and/or oscillating lights, strobe lights, an electronic display, an electronic projection, a siren, a loudspeaker, a bell, a vibrating device, etc., and any combination thereof. Accordingly, the claimed subject matter is not limited in scope in these respects.

The cabinet 104 may be a box like structure with an accessible area to provide access to the AED 102 such as, but not limited to, a cabinet with a transparent door, a cabinet with a breakable glass, a cabinet with a penetrable film or covering, etc., and any combination thereof. Additionally, it should be appreciated that use of the term cabinet is intended to be but one example, and accordingly, it is contemplated within the scope of the claimed subject matter that the AED 102 may be held in place by a wide variety of manners such as, but not limited to, a shelf, a transparent box, a self-adhesive manner, Velcro, etc., and any combination thereof. Further, in the system 100, the indicator device 106 may be shown as attached to the cabinet 104. However, it should be appreciated that it is contemplated within the scope of the claimed subject matter that the indicator device 106 may be separate from the cabinet (i.e., AED) and may be proximately located to the cabinet 104 (e.g., on an elevated pole, a platform, a separate wall, etc.). Accordingly, the claimed subject matter is not limited in these respects.

As previously described, it should be appreciated that the AED 102, may be but one example of an emergency apparatus contemplated within the scope of claimed subject matter. For example, emergency apparatus, which may be configured to help facilitate its location may include, but not limited to, gas masks, fire extinguishers, fire hydrants, etc. However, in order to describe the claimed subject matter, references may be made to an AED as but one non-limiting example.

As previously described, the emergency apparatus may be capable of transporting itself to the location where it is needed (e.g., with the help of a UAV). As may be appreciated, it is contemplated that the AED may, itself, have transportation capabilities such as, but not limited to, propulsion mechanisms such as, but not limited to, rotating blades to help propel itself to the location of the need.

Figure 2:
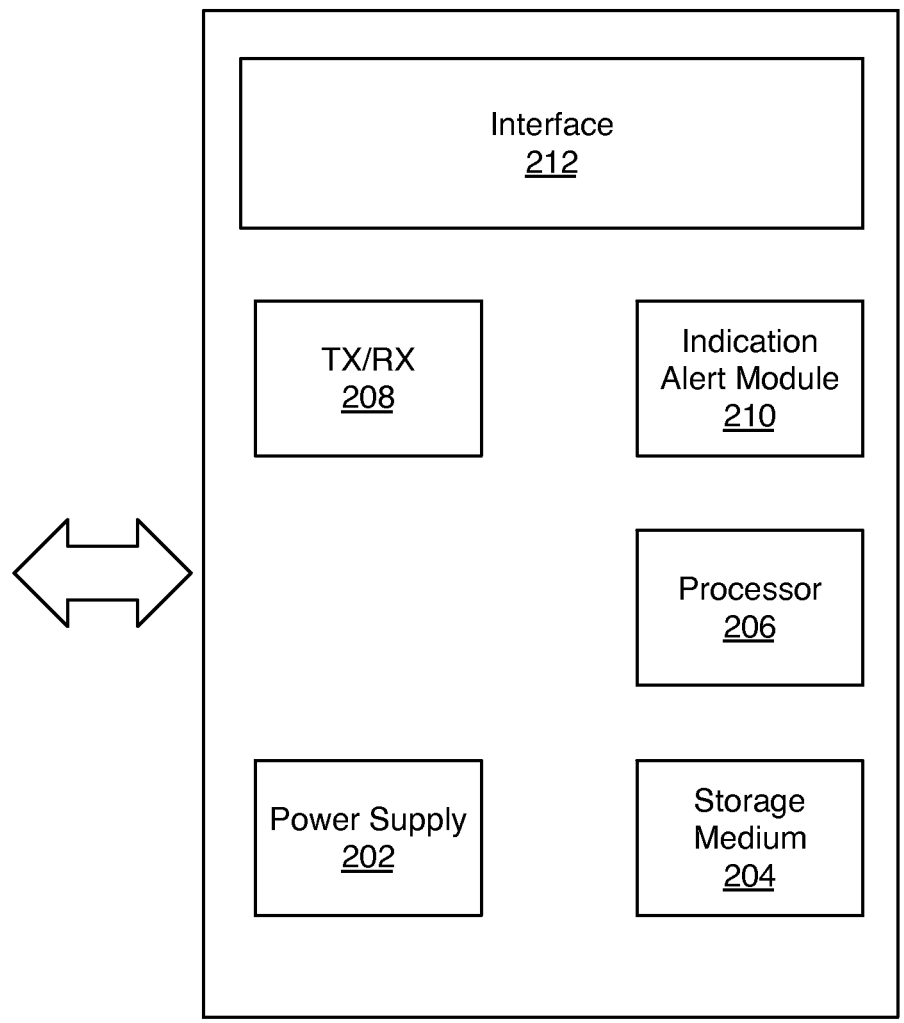
FIG. 2 illustrates a block diagram of an apparatus configured to indicate its location, in accordance with various embodiments.

FIG. 2 illustrates a block diagram of an emergency apparatus configured to indicate its location, in accordance with various embodiments. In FIG. 2, an emergency apparatus (e.g., an AED 200) is shown, which may be configured to indicate its location responsive to an indication that a person may be in need of an AED (PIN). The AED 200 may include various functional blocks such as, but not required or limited to, a power supply 202, a storage medium 204, a processor module 206, a transmit and/or receive module (TX/RX) 208, an indication alert module (IAM) 210 and a user interface 212.

In the example shown in FIG. 2, the AED 200 may receive an indication of a PIN via the TX/RX 206. The received indication may information regarding the location of the PIN. Working with the processor module 206 or independently, the AIM 210 may determine if the AED 200 is within a predetermined proximity to the PIN. The predetermined proximity information may be stored in the storage medium 204. The AIM 210 may determine whether the AED 200 is located within the predetermined proximity to the PIN based, at least in part, on the received indication and/or the location information regarding the location of the PIN. In one example, the information regarding the location may be in the form of GPS related information. If it is determined that the AED 200 is located within the predetermined proximity to the PIN, the AIM 210 may facilitate transmission of signal to an indicator device (e.g., indicator device 106 shown in FIG. 1). In one example, the signal may cause the indicator device 106 to emit a siren (i.e., an audio type indication). In another example, the signal may cause the indicator device 106 to activate a strobe (i.e., a visual type indication). Alternatively, the signal may cause the indicator device 106 to indicate utilizing any combination of audio type and/or visual type indication.

In one example, the AIM 210 may facilitate display of location information of the PIN relative to the AED 200 on the user interface 212. Accordingly, the user interface 212 may include a display capable of displaying mapping type applications. The mapping type applications may graphically indicate the location of the PIN and/or indication of one or more AEDs within the predetermined proximity of the PIN.

One example of the predetermined radius may be a radius of approximately 200 to 300 meters. In another example, the predetermined radius may be based, at least in part, on estimated time for a person to reach a person in need (PIN). Non-limiting examples may be include an estimated time of approximately 2 to 3 minutes for a pace of a brisk walk for an average person, an estimated time of approximately 2 to 3 minutes for a pace of a fast run, and/or any estimated time in between. In yet another example, the predetermined radius may be based, at least in part, on a time the emergency apparatus would need to self propel itself to the PIN. For example, the time the emergency apparatus would need to self propel itself to the PIN may depend upon a variety of factors such as, but not limited to, transportation capabilities of the UAV (e.g., velocity capabilities), environmental conditions (e.g., weather, wind, etc.), geographical conditions (e.g., obstructions and/or obstacles), and so forth.

It should be appreciated by those skilled in the art that in the example of a self propelled emergency apparatus, the received GPS information may be utilized for guidance to the location of the PIN and/or location where the emergency apparatus is needed.

In another example, some or all of the components/modules shown in FIG. 2 may be included in an emergency apparatus indicator device such as the indicator device 106 shown in FIG. 1. As previously described, an indicator device having some or all of the components/modules of FIG. 2 may receive a signal indicating that a person is in need of an AED (PIN). Responsive to the received indication, the indicator device 106 may activate.

Figure 3:
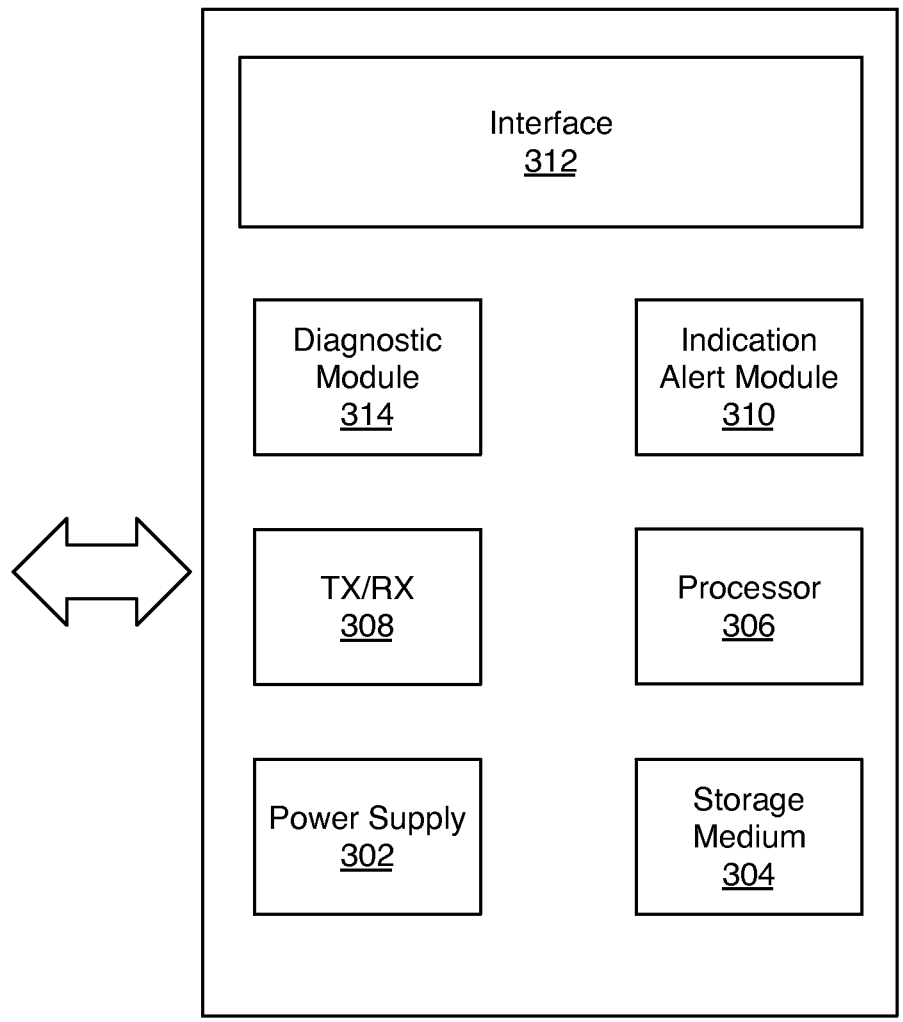
FIG. 3 illustrates a block diagram of an emergency apparatus configured to indicate its location, in accordance with another embodiment.

FIG. 3 illustrates a block diagram of an emergency apparatus configured to indicate its location, in accordance with another embodiment. In FIG. 3, an AED 300, may include various functional blocks similar those that may be found in the AED 200 (shown in FIG. 2). In the example shown in FIG. 3, the AED 300 may include various functional blocks such as, but not required or limited to, a power supply 302, a storage medium 304, a processor module 306, a transmit and/or receive module (TX/RX) 308, an indication alert module (IAM) 310, a user interface 312, and a self diagnostic module 314 in addition to or as an alternative to the various modules included and shown in FIG. 2.

In the example shown in FIG. 3, the AED 300 may receive an indication of a person in need of an AED (PIN) via the TX/RX 308. The received indication may include information regarding a location of the PIN. An example of information regarding the location of the PIN may be GPS information. Working with the processor module 306 or independently, the AIM 310 may determine if the AED 300 is within a predetermined proximity to the PIN. The predetermined proximity information may be stored in the storage medium 302. The IAM 310 may determine whether the AED 300 is located within the predetermined proximity to the PIN based, at least in part, on the received indication and/or the location information regarding the location of the PIN. If it is determined that the AED 300 is located within the predetermined proximity to the person in need, the IAM 310 may communicate with the diagnostic module 314 to determine if the AED 300 is capable of being used. The diagnostic module 314 may determine if the AED 300 is able to operate properly. For example, diagnostic module 314 may have the capabilities to determine a wide variety of diagnostic information such as, but not limited to, determine if the AED 300 has substantially sufficient electrical power to operate properly, determine if the shelf-life of the AED 300 has expired, determine if any of its components have degraded sitting on the shelf, determine if the electrodes have reached the end of its shelf life, and so forth. The variety of diagnostic information may be stored in the storage medium 304 and may be utilized by the diagnostic module 314 to help facilitate determination of diagnostic information of the AED 300.

The diagnostic module 314 may determine that the AED 300 is operationally ready for use, and accordingly, the diagnostic module 314 may communicate the determination to the IAM 310. The IAM 310 may, in turn, facilitate transmission of a signal to an indicator device (e.g., electronic indicator device 106 shown in FIG. 1). The transmitted signal may cause the electronic indicator device 106 to activate an indication of some kind (e.g., audible and/or visual) as previously described.

If, however, the diagnostic module 314 determines that, for at least any of the various reasons previously described, the AED 300 is not operationally ready for use, the IAM 310, in cooperation with the processor 306 or independently, may facilitate some form of indication on the interface 312. In one example, the interface 312 may display a message indicating not to use the AED 300 (e.g., "DO NOT USE"). In another example, the IAM 310 may, in cooperation with the processor 306 or independently, facilitate transmission of a signal to the indication device 106 to warn potential users that the AED 300 is not to be used (e.g., audio indication stating not to use the AED 300). In yet another example, the IAM 310 may, in cooperation with the processor 306 or independently, automatically prevent a transmission of a signal from the AED 300 to the indication device 106. In yet another example, upon determining that the AED 300 is not operationally ready for use, the IAM 310 may help facilitate the AED 300 from reacting to received indication of PIN (i.e., the AED 300 remains in a non-active state). Attempts to use the AED 300, which may not be operationally ready for use, may be prevented in various ways.

Figure 4:
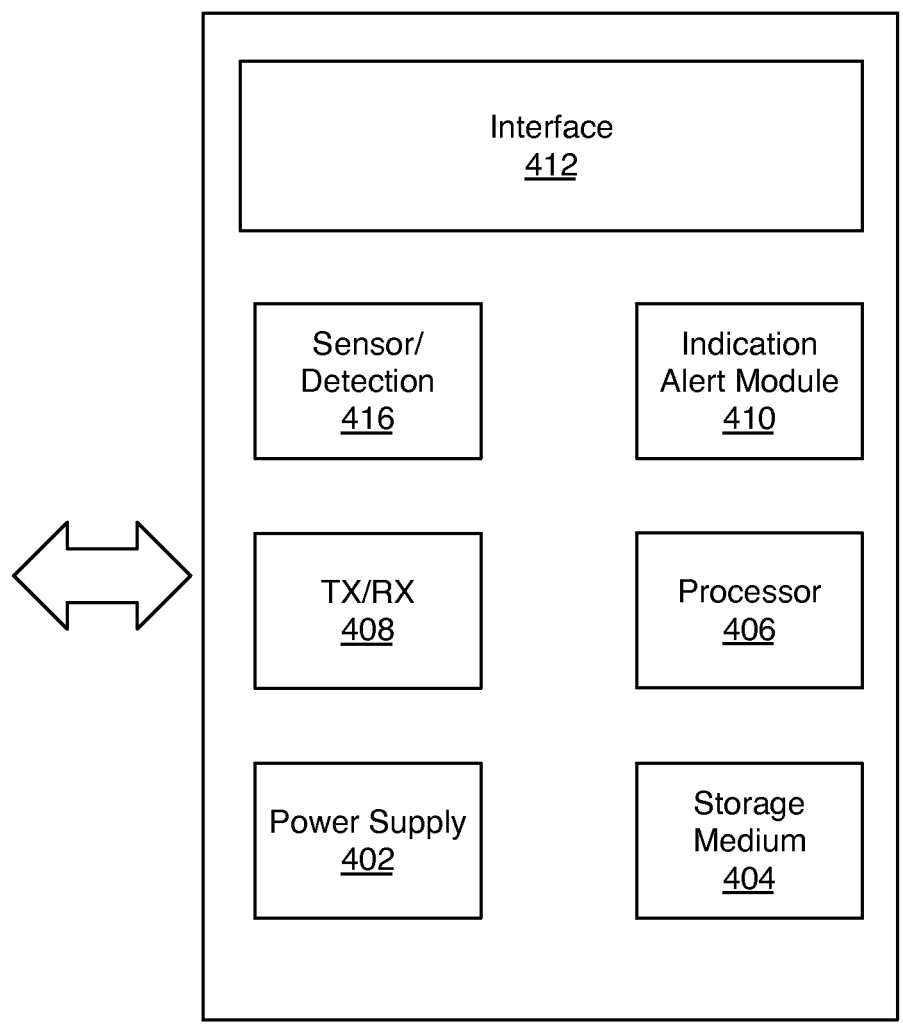
FIG. 4 illustrates a block diagram of an emergency apparatus configured to indicate its location, in accordance with yet another example.

FIG. 4 illustrates a block diagram of an emergency apparatus configured to indicate its location, in accordance with yet another example. In FIG. 4, an AED 400 may include various functional blocks similar those that may be found in the AED 200 and 300 (shown in FIGS. 2 and 3). In the example shown in FIG. 4, the AED 400 may include various functional blocks such as, but not required or limited to, a power supply 402, a storage medium 404, a processor module 406, a transmit and/or receive module (TX/RX) 408, an indication alert module (IAM) 410, a user interface 412, and a sensor/detector module 416 in addition to or as an alternative to the various modules included and shown in FIGS. 2 and 3.

In the example shown in FIG. 4, the AED 400 may indicate its position by interacting with a person passing by. The AED 400 may include functionality, where the AED 400 may be capable of being in a sleep mode and being awaken from the sleep mode if the sensor/detection module 416 detects motion. For example, the AED 400 may be in a sleep mode, where the user interface 412 may be inactive and/or blank. However, the sensor/detection module 416 may receive enough power (e.g., from the power supply 402) to function properly (i.e., detect motion). For example, the sensor/detection module 416 may include a passive infrared sensor type device, and when the sensor/detection module 416 detects a person passing by (i.e., detects motion of some kind), the sensor/detection module 416 may provide an indication to the IAM 410. In response to the received indication, IAM 410 may, in cooperation with the processor 406 or independently, cause the interface 412 to activate. In one example, the interface 412 may display a video showing a tutorial on the proper use of the AED 400. In another example, the AED 400 may already be in a state of notification that a person is in need of the AED 400 (i.e., visual and/or audio indication as previously described), and if the sensor/detection module 416 detects a person approaching, the interface 412 may display various information such as, but not limited to, how to properly use the AED 400, location information of the PIN (e.g., GPS mapping information), operational status of the AED 400 (e.g., battery charge level, information regarding expiration of the electrodes, etc.), time information (e.g., how long it has been since the person in need triggered the event), and so forth.

It should be appreciated that it is contemplated within the scope of the claimed subject matter that the AEDs 200, 300, and 400 may receive the indication of a person in need of the AEDs 200, 300, and 400 via a variety of methods. For example, the AEDs 200, 300, and 400 may receive indication via a wireless electronic communication medium. Some examples of a wireless communication medium may include, but not limited to, time-division multiple access (TDMA) communication technologies, frequency-division multiple access (FDMA) communication technologies, code-division multiple access (CDMA) communication technologies, orthogonal frequency division multiple access (OFDMA) communication technologies, and their multiple extensions and/or variations (e.g., long term evolution (LTE), universal mobile telecommunications system (UMTS), worldwide interoperability for microwave access (WiMAX), etc.). Some other examples of wireless communication mediums may include, but not limited to, near field communication (NFC) type electronic communication medium, radio-frequency identification (RFID) type of wireless electronic communication medium, Bluetooth wireless electronic communication medium, wireless local area network (WLAN) type wireless electronic communication medium (e.g., IEEE 802.11 and its variations and/or extensions), and so forth. Accordingly, the claimed subject matter is not limited in these respects.

Figure 5:
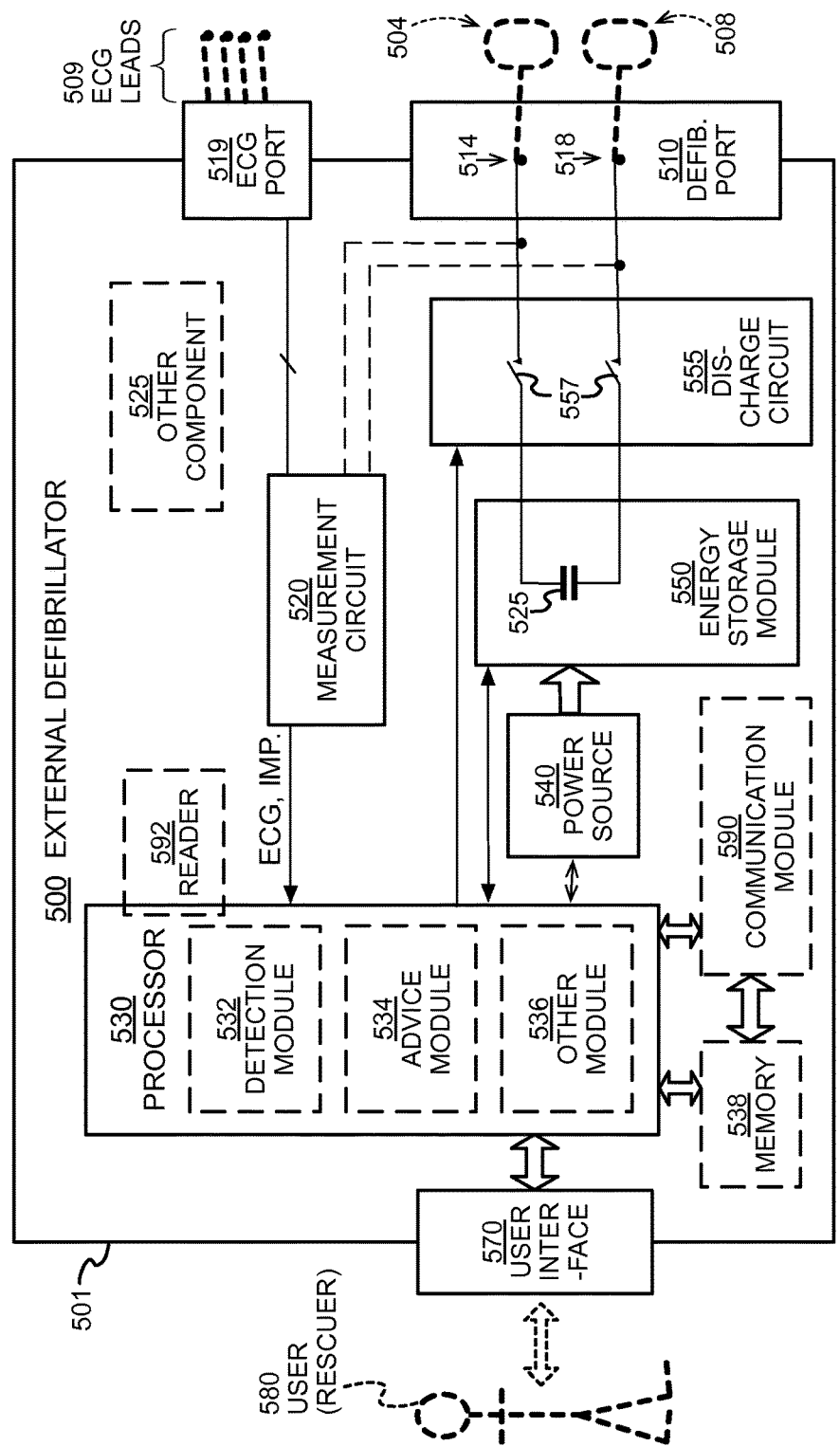
FIG. 5 is a block diagram illustrating components of defibrillator device, in accordance with various embodiments.

FIG. 5 is a block diagram illustrating components of defibrillator device 500, in accordance with various embodiments. These components may be, for example, a defibrillator device 102, 200, 300, and 400 (shown in FIGS. 1-4). Additionally, the components of FIGS. 2-4 may be provided in a housing 501, which may also be known as casing 501.

The defibrillator device 500 may be intended for use by a user 580 (e.g., a potential rescuer). The defibrillator device 500 may typically include a defibrillation port 510, such as a socket in housing 501. The defibrillation port 510 may include nodes 514 and 518. One or more electrodes 504 and 508 may be plugged in to the defibrillation port 510 facilitating an electrical contact with nodes 514 and 518, respectively. It may also be possible that the electrodes 504 and 508 may be connected continuously to the defibrillation port 510, etc. The defibrillation port 510 may be used to facilitate guidance, via the electrodes 504 and 508, to a PIN an electrical charge that may have been stored in the defibrillator device 500, as described herein. As previously described, some, any, all, or any combination thereof of the components/modules illustrated in FIGS. 2-4 may be included in the defibrillator device 500 and may provide the various functionalities and/or any combination of functionalities described herein.

If the defibrillator device 500 comprises of a defibrillator-monitor (e.g., interface 212, 312, and 412 of FIGS. 2-4), the defibrillator device 500 may also include an ECG port 519 in the housing 501, for receiving ECG leads 509. The ECG leads 509 may facilitate sensing of an ECG signal (e.g., a 12-lead signal or from a different number of lead signals). Moreover, a defibrillator-monitor may have additional ports (not shown), and the other component 525 may be configured to filter the ECG signal (e.g., application of at least one filter to the signal to help facilitate removal of artifacts such as, but not limited to, chest compression due to chest compressions being delivered to the person in need of an AED).

The defibrillator 500 also may include a measurement circuit 520. The measurement circuit 520 may receive physiological signals from the ECG port 519, and also from other ports, if provided. The measurement circuit 520 may render detected physiological signals and their corresponding information. The information may be in the form of data, or other signals, etc.

If the defibrillator 500 may be configured as an AED type device as but one non-limiting example, ECG port 519 may not be present. The measurement circuit 520 may obtain physiological signals through the nodes 514 and 518 instead, when the electrodes 504 and 508 are attached to the person in need of the AED. In these cases, a person's ECG signal may be detected as a voltage difference between the electrodes 504 and 508. Additionally, the impedance between the electrodes 504 and 508 may detect, among other things, whether the electrodes 504 and 508 have been inadvertently disconnected from the PIN.

The defibrillator 500 may also include a processor 530 such as those described with respect to FIGS. 2-4 (e.g., processor 206, 306, and 406). The processor 530 may be implemented in a wide variety of manners for causing actions and operations to be performed and described herein. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 530 may include a number of modules. One example module may be a detection module 532, which may detect outputs from the measurement circuit 520. The detection module 532 may include a VF detector. Accordingly, a person's detected ECG may be utilized to help determine whether the person is experiencing VF.

In another example, advice module 534 may provide advice based, at least in part, on outputs of the detection module 532. The advice module 534 may include an algorithm such as, but not limited to, Shock Advisory Algorithm, implement decision rules, and so on. For example, the advice may be to shock, to not shock, to administer other forms of therapy, and so forth. If the advice is to shock, some defibrillator examples may report the advice to the user and prompt them to do it. In other examples, the defibrillator device may execute the advice by administering the shock. If the advice is to administer CPR, the defibrillator 300 may further issue prompts for administrating CPR, and so forth.

The processor 530 may include additional modules, such as module 536 for various functions as described herein. For example, the other module 536 may be a module for facilitating transmission of a signal to a location indicator (e.g., IAM 210, 310, and 410 such as those described with respect to FIGS. 2-4). In another example, the other module 536 may be a module for facilitating diagnostic determination of the defibrillator 500 (e.g., diagnostic module 314 as described in FIG. 3). In yet another example, the other module 536 may be a module for facilitating detection and/or sensing a person/motion (e.g., sensor/detection module 416 as described with respect to FIG. 4).

In an example, the defibrillator device 500 may include a memory 538 (e.g., storage medium 204, 304, and 404 shown in FIGS. 2-4), which may work together with the processor 530. The memory 538 may be implemented in a wide variety of manners. For example, the memory 538 may be implemented such as, but not limited to, nonvolatile memories (NVM), read-only memories (ROM), random access memories (RAM), and so forth or any combination thereof. The memory 538 may include programs for the processor 530, and so on. The programs may include operational programs executed by the processor 530 and may also include protocols and methodologies so that decisions may be made by advice module 534. Additionally, the memory 538 may store various prompts for the user 580, etc. Moreover, the memory 538 may store a wide variety of information (i.e., data) such as, but not limited to information regarding the PIN.

The defibrillator 500 may also include a power source 540 such as, but not limited to, those shown in FIGS. 2-4 (power supply 202, 302, and 402). In order to facilitate portability of defibrillator device 500, the power source 540 may include a battery type device. A battery type device may be implemented as a battery pack, which may be rechargeable or non-rechargeable. At times, a combination of rechargeable and non-rechargeable battery packs may be utilized. Examples of power source 540 may include AC power override, where AC power may be available, and so on. In some examples, the processor 530 may control the power source 540. As previously described, in one example, the power source 540 may provide power to the sensor detection module 416 to facilitate detection of motion as described with respect to FIG. 4.

Additionally, the defibrillator device 500 may include an energy storage module 550. The energy storage module 550 may be configured to store some electrical energy (e.g., when preparing for sudden discharge to administer a shock). The energy storage module 550 may be charged from the power source 540 to an appropriate level of energy, as may be controlled by the processor 530. In some implementations, the energy storage module 550 may include one or more capacitors 552, and the like.

The defibrillator 500 may include a discharge circuit 555. The discharge circuit 555 may be controlled to facilitate discharging of the energy stored in energy storage module 550 to the nodes 514 and 518, and also to electrodes 304 and 308. The discharge circuit 555 may include one or more switches 557. The one or more switches 557 may be configured in a number of manners such as, but not limited to, an H-bridge, and so forth.

The defibrillator device 500 may further include a user interface 570 such as, but not limited to, those described with respect to FIGS. 2-4 (interface 212, 312, and 412) for the user 580. The user interface 570 may be implemented in a variety of manners. For example, the user interface 570 may include a display screen capable of displaying what is detected and measured, provide visual feedback to the user 580 for their resuscitation attempts, and so forth. The user interface 570 may also include an audio output such as, but not limited to, a speaker to issue audio prompts, etc. The user interface 570 may additionally include various control devices such as, but not limited to, pushbuttons, keyboards, switches, track pads, and so forth. Additionally, the discharge circuit 555 may be controlled by the processor 530 or directly by the user 580 via the user interface 570, and so forth.

Additionally, the defibrillator device 500 may include other components. For example, a communication module 590 may be provided for communicating with other machines and/or other services such as, but not limited to, those communication as previously described with respect to FIGS. 1-4 (TX/RX 208, 304, and 404 shown in FIGS. 2-4). Such communication may be performed wirelessly, or via wire, or by infrared communication, near field communication (NFC), Bluetooth, Wi-Fi, and so forth. Accordingly, information may be communicated, such as person data, incident information, therapy attempted, CPR performance, ECG information, and so forth.

Figure 6:
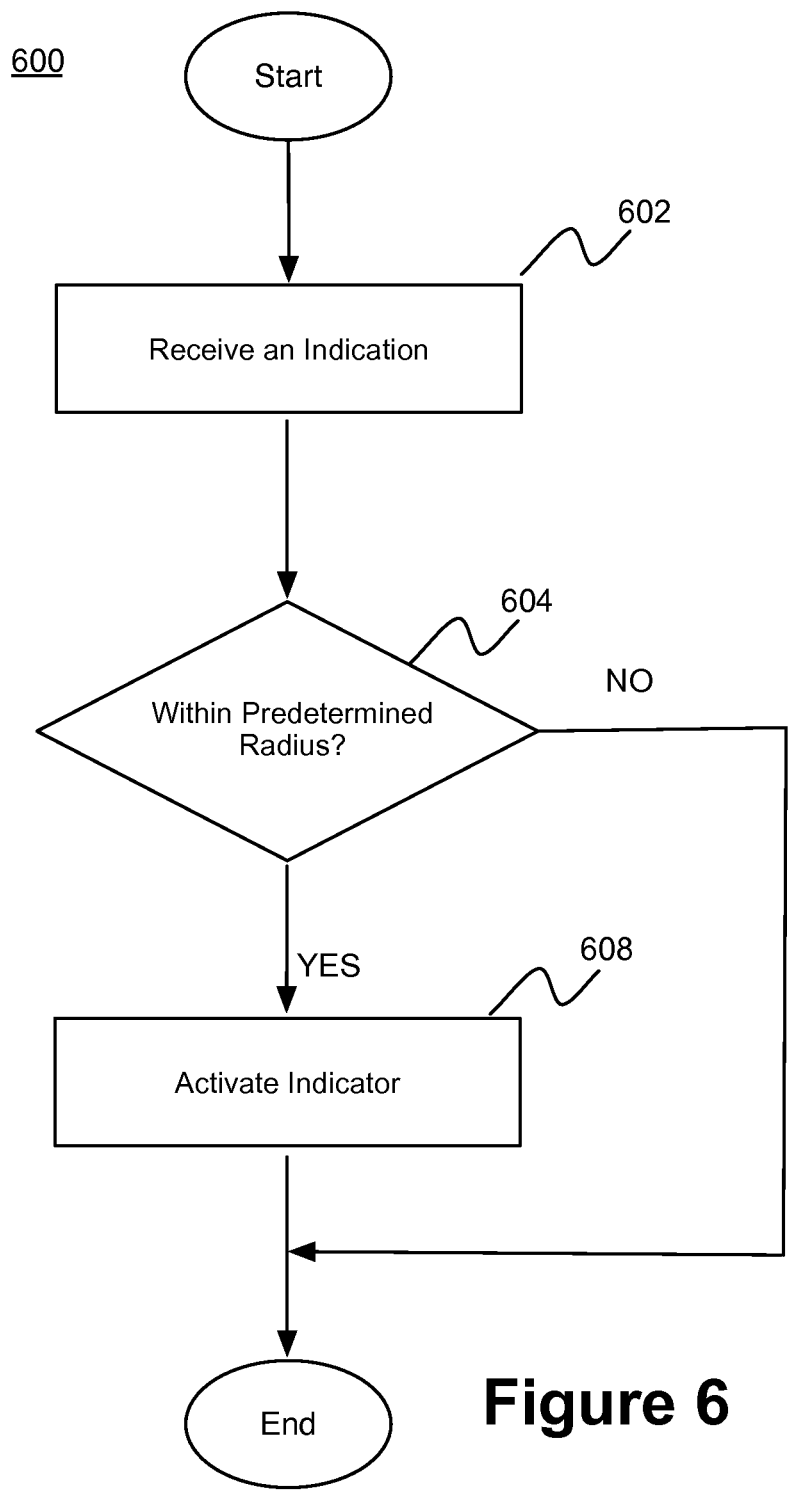
FIG. 6 illustrate an operational flow for an emergency apparatus capable of indicating its location, arranged in accordance with at least some embodiments.

FIG. 6 illustrate an operational flow for an emergency apparatus capable of indicating its location, arranged in accordance with at least some embodiments described herein. In some portions of the description, illustrative implementations of the method are described with reference to the elements of apparatuses depicted in FIGS. 1, 2, 3, 4, and 5. However, the described embodiments are not limited to these depictions. More specifically, some elements depicted in FIGS. 1, 2, 3, 4, and 5 may be omitted from some implementations of the methods details herein. Furthermore, other elements not depicted in FIGS. 1, 2, 3, 4, and 5 may be used to implement example methods detailed herein.

Additionally, FIG. 6 employs block diagrams to illustrate the example methods detailed therein. These block diagrams may set out various functional block or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of the claimed subject matter.

In some examples, operational flow 600 may be employed as part of an indication alert module. Beginning at block 602

("Receive an Indication"), an emergency apparatus (e.g., emergency apparatus 102, 200, 300, 400, and 500 as shown in FIGS. 1, 2, 3, 4, and 5) and/or an electronic indicator device (e.g., the electronic indicator device 106 as shown in FIG. 1) may receive, via an electronic communication medium, an indication of a need for an emergency apparatus. The indication may include information regarding a location of the need. A non-limiting example of information regarding the location of the need may be GPS information. The electronic communication medium may include a wide variety of electronic communication medium such as, but not limited to wireless and/or wired electronic communication medium. As previously described, the indication may be received by a transmit and/or receive module (e.g., TX/RX 208, 308, 408, and communication module 590 as shown in FIGS. 2, 3, 4, and 5) communicatively coupled to the emergency apparatus.

Continuing from block 602 to block 604 ("Within Predetermined Radius?"), an indication alert module (e.g., IAM 210, 310, and 410 as shown in FIGS. 2, 3, and 4) may determine if the location of the need for the emergency apparatus is within a predetermined radius relative to the emergency apparatus. The determination may be based, at least in part, on the information regarding the location of the need. The information may be received in a wide variety of manner dependent, at least in part, on the electronic communication medium such as, but not limited to wireless and/or wired electronic communication medium including information which may be stored in a storage medium.

As previously described, one example of the predetermined radius may be a radius of approximately 200 to 300 meters. In another example, the predetermined radius may be based, at least in part, on estimated time for a person to reach a person in need (PIN). Non-limiting examples may be include an estimated time of approximately 2 to 3 minutes for a pace of a brisk walk for an average person, an estimated time of approximately 2 to 3 minutes for a pace of a fast run, and/or any estimated time in between.

Continuing from block 604 to block 608 ("Activate Indicator"), if it is determined that the location of the need is within the predetermined radius, the electronic indicator device (e.g., electronic indicator device 106 as shown in FIG. 1) may be activated. As previously described, in one non-limiting example, the electronic indicator device may be communicatively coupled with the emergency apparatus. If on the other hand, if it is determined that the location of the need is not within the predetermined radius, the electronic indicator may not be activated, and the emergency apparatus and/or the electronic indicator device may remain as is (i.e., not drawing attention to itself).

In general, the operational flow described with respect to FIG. 6 and elsewhere herein may be implemented as a computer program product, executable on any suitable computing system, or the like. For example, a computer program product for facilitating indication of a location of an electronic emergency device may be provided. Example computer program products may be described with respect to FIG. 9 and elsewhere herein.

It should be appreciated that information regarding the location of the PIN may be include mapping information such as, but not limited to, static mapping information, interactive mapping, voice recognition information (e.g., recognizing such audio information as "corner of 12$^{th}$ and Yamhill), global positioning system (GPS) information, and so forth.

Figure 7:
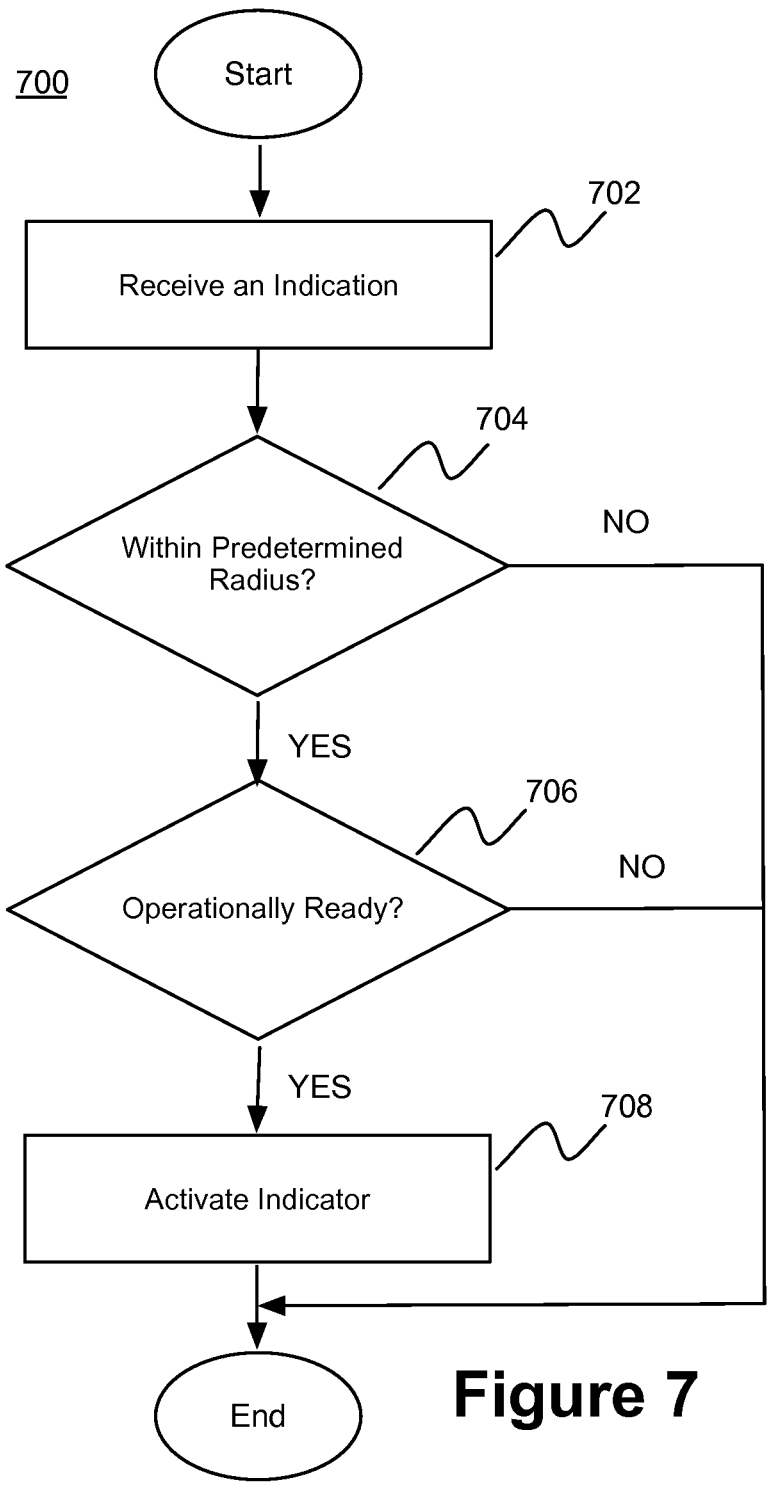
FIG. 7 illustrate an operational flow for an emergency apparatus capable of indicating its location, arranged in accordance with at least some embodiments.

FIG. 7 illustrate an operational flow for an emergency apparatus capable of indicating its location, arranged in accordance with at least some embodiments described herein. In some portions of the description, illustrative implementations of the method are described with reference to the elements of electronic emergency apparatus depicted in FIGS. 1, 2, 3, 4, and 5. However, the described embodiments are not limited to these depictions. More specifically, some elements depicted in FIGS. 1, 2, 3, 4, and 5 may be omitted from some implementations of the methods details herein. Furthermore, other elements not depicted in FIGS. 1, 2, 3, 4, and 5 may be used to implement example methods detailed herein.

Additionally, FIG. 7 employs block diagrams to illustrate the example methods detailed therein. These block diagrams may set out various functional block or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of the claimed subject matter.

In some examples, operational flow 700 may be employed as part of an indication alert module. Beginning at block 702 ("Receive an Indication"), an emergency apparatus (e.g., emergency apparatus 102, 200, 300, 400, and 500 as shown in FIGS. 1, 2, 3, 4, and 5) may receive, via an electronic communication medium, an indication of a need for the emergency apparatus. The indication may include information regarding a location of the need. The electronic communication medium may include a wide variety of electronic communication medium such as, but not limited to wireless and/or wired electronic communication medium. As previously described, the indication may be received by a transmit and/or receive module (e.g., TX/RX 208, 308, 408, and communication module 590 as shown in FIGS. 2, 3, 4, and 5) communicatively coupled to the emergency apparatus.

Continuing from block 702 to block 704 ("Within Predetermined Radius?"), an indication alert module (e.g., IAM 210, 310, and 410 as shown in FIGS. 2, 3, and 4) may determine if the location of the need for the emergency apparatus is within a predetermined radius relative to the emergency apparatus. The determination may be based, at least in part, on the information regarding the location of the need. The information may be received in a wide variety of manner dependent, at least in part, on the electronic communication medium such as, but not limited to wireless and/or wired electronic communication medium including a storage medium.

As previously described, one example of the predetermined radius may be a radius of approximately 200 to 300 meters. In another example, the predetermined radius may be based, at least in part, on estimated time for a person to reach a person in need (PIN). Non-limiting examples may be include an estimated time of approximately 2 to 3 minutes for a pace of a brisk walk for an average person, an estimated time of approximately 2 to 3 minutes for a pace of a fast run, and/or any estimated time in between. Additionally, in the case of the self propelled emergency apparatus, the time the emergency apparatus would need to self propel itself to the PIN may be utilized to determine the predetermined radius as previously described (e.g., transportation capabilities, environmental conditions, geographical conditions, and so forth.

Continuing from block 704 to block 706 ("Operationally Ready?"), a diagnostic module (e.g., diagnostic module 314 as shown in FIG. 3) may determine if the emergency apparatus is operationally ready for use. As previously described with respect to FIG. 3, the operational status of the emergency apparatus may include operational status such as, but not limited to, a power supply level (e.g., battery charge) of the emergency apparatus and/or information regarding expiration of one or more electrodes associated with the emergency apparatus. Some other examples of operational status may include, but not limited to, expiration of various material (e.g., chemicals) associated with the emergency apparatus and/or time information (e.g., how long it has been since the person in need triggered the event) to determine if the emergency apparatus may no longer be needed. Some other examples of operational status may include, but not limited to, certification information (e.g., time since the last inspection of the emergency apparatus), mechanical status information (e.g., pressure level), and/or any operational status or the emergency apparatus.

Continuing from block 706 to block 708 ("Activate Indicator"), if it is determined that the location of the need is within the predetermined radius and that the emergency apparatus is operationally ready for use, an electronic indicator device (e.g., electronic indicator device 106 as shown in FIG. 1) may be activated. The electronic indicator device may be communicatively coupled with the emergency apparatus, as previously described. If on the other hand, if it is determined that the location of the need is not within the predetermined radius and/or the emergency apparatus is not operationally ready for use the electronic indicator may not be activated, and the emergency may remain as is (i.e., not drawing attention to itself).

In general, the operational flow described with respect to FIG. 7 and elsewhere herein may be implemented as a computer program product, executable on any suitable computing system, or the like. For example, a computer program product for facilitating indication of a location of an electronic emergency device may be provided. Example computer program products may be described with respect to FIG. 10 and elsewhere herein.

It should be appreciated that information regarding the location of the PIN may be include mapping information such as, but not limited to, static mapping information, interactive mapping, voice recognition information (e.g., recognizing such audio information as "corner of 12$^{th}$ and Yamhill), global positioning system (GPS) information, and so forth.

Figure 8:
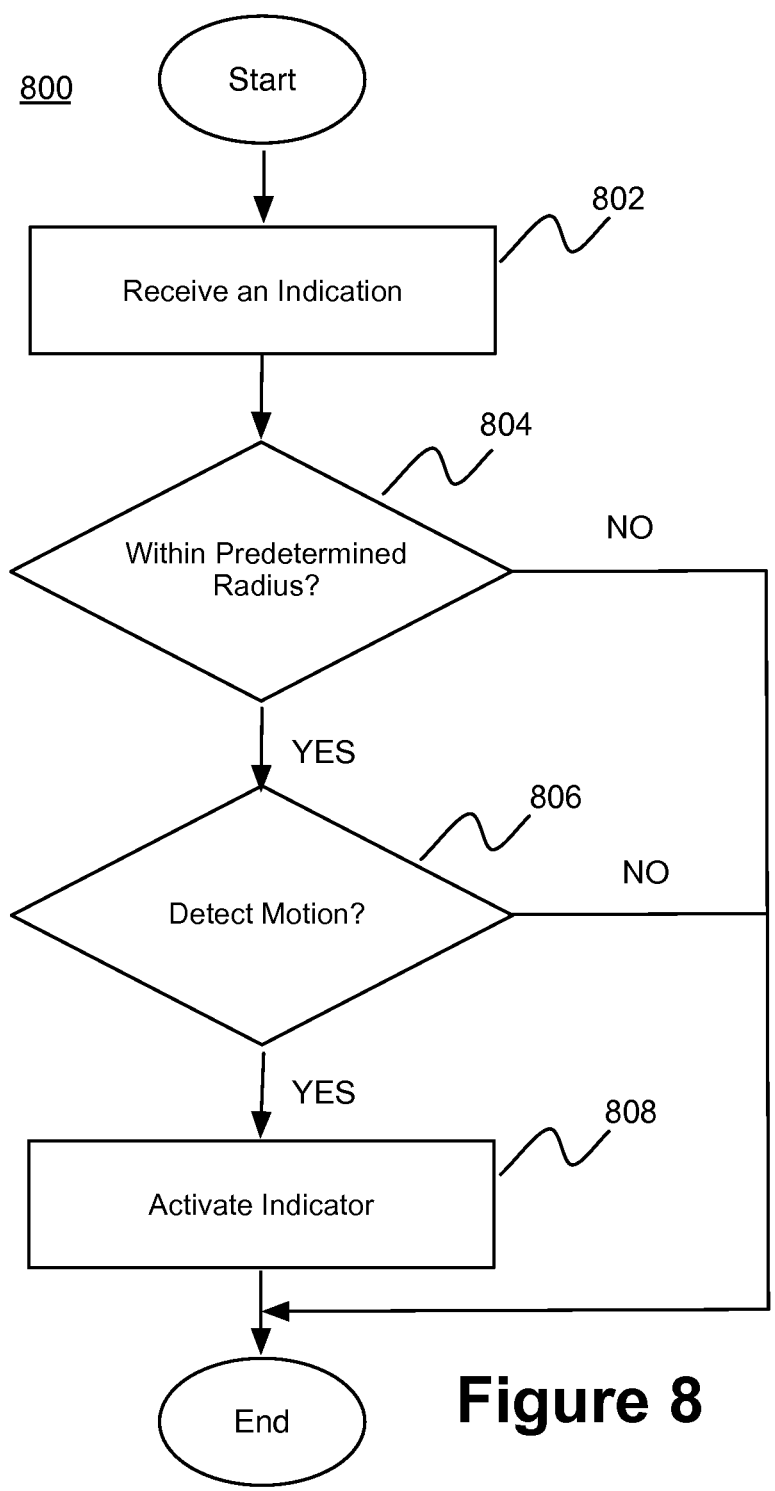
FIG. 8 illustrate an operational flow for an emergency apparatus capable of indicating its location, arranged in accordance with at least some embodiments.

FIG. 8 illustrates an operational flow for an emergency apparatus capable of indicating its location, arranged in accordance with at least some embodiments described herein. In some portions of the description, illustrative implementations of the method are described with reference to the elements of electronic emergency apparatus depicted in FIGS. 1, 2, 3, 4, and 5. However, the described embodiments are not limited to these depictions. More specifically, some elements depicted in FIGS. 1, 2, 3, 4, and 5 may be omitted from some implementations of the methods details herein. Furthermore, other elements not depicted in FIGS. 1, 2, 3, 4, and 5 may be used to implement example methods detailed herein.

Additionally, FIG. 8 employs block diagrams to illustrate the example methods detailed therein. These block diagrams may set out various functional block or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of the claimed subject matter.

In some examples, operational flow 800 may be employed as part of an indication alert module. Beginning at block 802 ("Receive an Indication"), an emergency apparatus (e.g., emergency apparatus 102, 200, 300, 400, and 500 as shown in FIGS. 1, 2, 3, 4, and 5) may receive, via an electronic communication medium, an indication of a need for the emergency apparatus. The indication may include information regarding a location of the need. The electronic communication medium may include a wide variety of electronic communication medium such as, but not limited to wireless and/or wired electronic communication medium. As previously described, the indication may be received by a transmit and/or receive module (e.g., TX/RX 208, 308, 408, and communication module 590 as shown in FIGS. 2, 3, 4, and 5) communicatively coupled to the emergency apparatus.

Continuing from block 802 to block 804 ("Within Predetermined Radius?"), an indication alert module (e.g., IAM 210, 310, and 410 as shown in FIGS. 2, 3, and 4) may determine if the location of the need for the emergency apparatus is within a predetermined radius relative to the emergency apparatus. The determination may be based, at least in part, on the information regarding the location of the need. The information may be received in a wide variety of manner dependent, at least in part, on the electronic communication medium such as, but not limited to wireless and/or wired electronic communication medium including a storage medium.

As previously described, one example of the predetermined radius may be a radius of approximately 200 to 300 meters. In another example, the predetermined radius may be based, at least in part, on estimated time for a person to reach a person in need (PIN). Non-limiting examples may be include an estimated time of approximately 2 to 3 minutes for a pace of a brisk walk for an average person, an estimated time of approximately 2 to 3 minutes for a pace of a fast run, and/or any estimated time in between.

Additionally, in the case of the self propelled emergency apparatus, the time the emergency apparatus would need to self propel itself to the PIN may be utilized to determine the predetermined radius as previously described (e.g., transportation capabilities, environmental conditions, geographical conditions, and so forth.

Continuing from block 804 to block 806 ("Detect Motion?"), a motion detector (e.g., sensor/motion detector module 416 as shown in FIG. 4) may determine if motion is detected proximate to the emergency apparatus. As previously described, the emergency apparatus may be capable of being in a sleep mode and being awaken from the sleep mode if the motion detector detects motion. For example, the emergency apparatus may be in a sleep mode, where a user interface (e.g., interface 212, 312, 412, and 570 as shown in FIGS. 2, 3, 4, and 5) may be inactive and/or blank. However, the motion detector may receive enough power (e.g., from a power supply such as power supply 202, 302, 402, and 540 as shown in FIGS. 2, 3, 4, and 5) to function properly (i.e., detect motion). For example, the motion detector may include a passive infrared sensor type device, and when the motion detector detects a person passing by (i.e., detects motion of some kind), the motion detector may provide an indication to an indication module (e.g., IAM 210, 310, 410 as shown in FIGS. 2, 3, and 4). In response to the received indication, the indication module may cause the user interface to activate. In one example, the user interface may display a video showing a tutorial on the proper use of the emergency apparatus. In another example, the emergency apparatus may already be in a state of notification that a person is in need of the emergency apparatus (i.e., visual and/or audio indication as previously described), and if the motion detector detects a person approaching, the user interface may display various information such as, but not limited to, how to properly use the emergency apparatus, location information of the PIN (e.g., GPS mapping information), operational status of the emergency apparatus (e.g., battery charge level, information regarding expiration of the electrodes, etc.), time information (e.g., how long it has been since the person in need triggered the event), and so forth as previously described.

Continuing from block 806 to block 808 ("Activate Indicator"), if it is determined that the location of the need is within the predetermined radius and/or that motion is detected, an electronic indicator device (e.g., electronic indicator device 106 as shown in FIG. 1) may be activated. The electronic indicator device being communicatively coupled with the emergency apparatus. If on the other hand, if it is determined that the location of the need is not within the predetermined radius and/or motion is not detected, the electronic indicator may not be activated, and the emergency may remain as is (i.e., not drawing attention to itself).

In general, the operational flow described with respect to FIG. 8 and elsewhere herein may be implemented as a computer program product, executable on any suitable computing system, or the like. For example, a computer program product for facilitating indication of a location of an electronic emergency device may be provided. Example computer program products may be described with respect to FIG. 11 and elsewhere herein.

It should be appreciated that information regarding the location of the PIN may be include mapping information such as, but not limited to, static mapping information, interactive mapping, voice recognition information (e.g., recognizing such audio information as "corner of 12$^{th}$ and Yamhill), global positioning system (GPS) information, and so forth.

FIG. 9 illustrates an example computer program product 900, arranged in accordance with at least some embodiments described herein. Computer program product 900 may include machine readable non-transitory medium having stored therein instructions that, when executed, cause the machine to facilitate indication of a location of an emergency apparatus, according to the processes and methods discussed herein. Computer program product 900 may include a signal bearing medium 902. Signal bearing medium 902 may include one or more machine-readable instructions 904 which, when executed by one or more processors, may operatively enable a computing device to provide the functionality described herein. In various examples, the devices discussed herein may use some or all of the machine-readable instructions.

In some examples, the machine readable instructions 904 may include instructions to receive at an emergency apparatus, via an electronic communication medium, an indication of a need for the emergency apparatus, where the indication may include information regarding a location of the need. In some examples, the machine readable instructions 904 may include instructions to determine if the location of the need is within a predetermined radius relative to a location of the emergency apparatus, the determine based, at least in part, on the information regarding the location of the need. In some examples, the machine readable instructions 904 may include instructions to, if it is determined that the location of the need is within the predetermined radius, activate an electronic indicator device, the electronic indicator device being communicatively coupled to the emergency apparatus.

In some implementations, signal bearing medium 902 may encompass a computer-readable medium 906, such as, but not limited to, a hard disk drive, a Compact Disc (CD), a Digital Versatile Disk (DVD), a Universal Serial Bus (USB) drive, a digital tape, memory, etc. In some implementations, the signal bearing medium 902 may encompass a recordable medium 908, such as, but not limited to, memory, read/write (R/W) CDs, R/W DVDs, etc. In some implementations, the signal bearing medium 902 may encompass a communications medium 910, such as, but not limited to, a digital and/or an analog communication medium (e.g., a fiber optic cable, a waveguide, a wired communication link, a wireless communication link, etc.). In some examples, the signal bearing medium 902 may encompass a machine readable non-transitory medium.

FIG. 10 illustrates an example computer program product 1000, arranged in accordance with at least some embodiments described herein. Computer program product 1000 may include machine readable non-transitory medium having stored therein instructions that, when executed, cause the machine to facilitate indication of a location of an emergency apparatus, according to the processes and methods discussed herein. Computer program product 1000 may include a signal bearing medium 1002. Signal bearing medium 1002 may include one or more machine-readable instructions 1004 which, when executed by one or more processors, may operatively enable a computing device to provide the functionality described herein. In various examples, the devices discussed herein may use some or all of the machine-readable instructions.

In some examples, the machine readable instructions 1004 may include instructions to receive at an emergency apparatus, via an electronic communication medium, an indication of a need for the emergency apparatus, where the indication may include information regarding a location of the need. In some examples, the machine readable instructions 1004 may include instructions to determine if the location of the need is within a predetermined radius relative to a location of the emergency apparatus, the determine based, at least in part, on the information regarding the location of the need. In some examples, the machine readable instructions 1004 may include instructions to determine if the emergency apparatus is operationally ready for use. In some examples, the machine readable instructions 1004 may include instructions to, if it is determined that the location of the need is within the predetermined radius and that the emergency apparatus is operationally ready for use, activate an electronic indicator device, the electronic indicator device being communicatively coupled to the emergency apparatus.

In some implementations, signal bearing medium 1002 may encompass a computer-readable medium 1006, such as, but not limited to, a hard disk drive, a Compact Disc (CD), a Digital Versatile Disk (DVD), a Universal Serial Bus (USB) drive, a digital tape, memory, etc. In some implementations, the signal bearing medium 1002 may encompass a recordable medium 1008, such as, but not limited to, memory, read/write (R/W) CDs, R/W DVDs, etc. In some implementations, the signal bearing medium 1002 may encompass a communications medium 1010, such as, but not limited to, a digital and/or an analog communication medium (e.g., a fiber optic cable, a waveguide, a wired communication link, a wireless communication link, etc.). In some examples, the signal bearing medium 1002 may encompass a machine readable non-transitory medium.

FIG. 11 illustrates an example computer program product 1100, arranged in accordance with at least some embodiments described herein. Computer program product 1100 may include machine readable non-transitory medium having stored therein instructions that, when executed, cause the machine to facilitate indication of a location of an emergency apparatus, according to the processes and methods discussed herein. Computer program product 1100 may include a signal bearing medium 1102. Signal bearing medium 1102 may include one or more machine-readable instructions 1104 which, when executed by one or more processors, may operatively enable a computing device to provide the functionality described herein. In various examples, the devices discussed herein may use some or all of the machine-readable instructions.

In some examples, the machine readable instructions 1104 may include instructions to receive at an emergency apparatus, via an electronic communication medium, an indication of a need for the emergency apparatus, where the indication may include information regarding a location of the need. In some examples, the machine readable instructions 1104 may include instructions to determine if the location of the need is within a predetermined radius relative to a location of the emergency apparatus, the determine based, at least in part, on the information regarding the location of the need. In some examples, the machine readable instructions 1104 may include instructions to determine if motion is detected proximate to the emergency apparatus. In some examples, the machine readable instructions 1104 may include instructions to, if it is determined that the location of the need is within the predetermined radius and/or that motion is detected, the electronic indicator device being communicatively coupled to the emergency apparatus.

In some implementations, signal bearing medium 1102 may encompass a computer-readable medium 1106, such as, but not limited to, a hard disk drive, a Compact Disc (CD), a Digital Versatile Disk (DVD), a Universal Serial Bus (USB) drive, a digital tape, memory, etc. In some implementations, the signal bearing medium 1102 may encompass a recordable medium 1108, such as, but not limited to, memory, read/write (R/W) CDs, R/W DVDs, etc. In some implementations, the signal bearing medium 1102 may encompass a communications medium 1110, such as, but not limited to, a digital and/or an analog communication medium (e.g., a fiber optic cable, a waveguide, a wired communication link, a wireless communication link, etc.). In some examples, the signal bearing medium 1102 may encompass a machine readable non-transitory medium.

In general, the methods described with respect to FIGS. 6, 7, 8, and elsewhere herein may be implemented in any suitable computing system. Example systems may be described with respect to FIG. 12 and elsewhere herein. In general, the system may be configured to facilitate indication of a location of an emergency apparatus.

Figure 12:
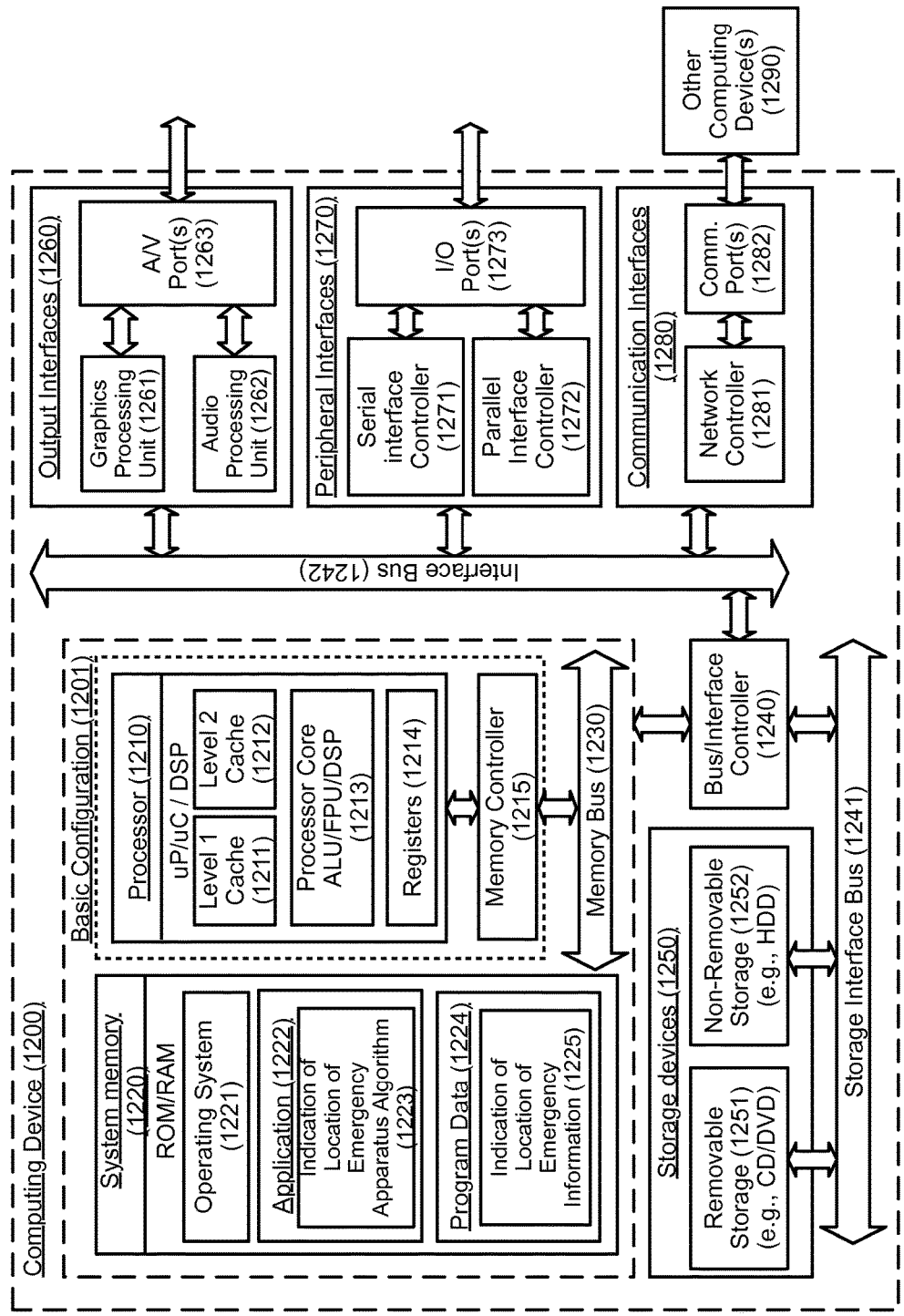
FIG. 12 is a block diagram illustrating an example computing device 1200, such as might be embodied by a person skilled in the art, which is arranged in accordance with at least some embodiments.

FIG. 12 is a block diagram illustrating an example computing device 1200, such as might be embodied by a person skilled in the art, which is arranged in accordance with at least some embodiments of the present disclosure. In one example configuration 1201, computing device 1200 may include one or more processors 1210 and system memory 1220. A memory bus 1230 may be used for communicating between the processor 1210 and the system memory 1220.

Depending on the desired configuration, processor 1210 may be of any type including but not limited to a microprocessor (µP), a microcontroller (µC), a digital signal processor (DSP), or any combination thereof. Processor 1210 may include one or more levels of caching, such as a level one cache 1211 and a level two cache 1212, a processor core 1213, and registers 1214. The processor core 1213 may include an arithmetic logic unit (ALU), a floating point unit (FPU), a digital signal processing core (DSP Core), or any combination thereof. A memory controller 1215 may also be used with the processor 1210, or in some implementations the memory controller 1215 may be an internal part of the processor 1210.

Depending on the desired configuration, the system memory 1220 may be of any type including but not limited to volatile memory (such as RAM), non-volatile memory (such as ROM, flash memory, etc.) or any combination thereof. System memory 1220 may include an operating system 1221, one or more applications 1222, and program data 1224. Application 1222 may include indication of a location of an emergency apparatus configuration algorithm 1223 that is arranged to perform the functions as described herein including the functional blocks and/or actions described. Program Data 1224 may include, among a wide variety of information described, indication of a location of an emergency apparatus information 1225 for use with indication of a location of an emergency apparatus algorithm 1223. In some example embodiments, application 1222 may be arranged to operate with program data 1224 on an operating system 1221 such that implementations of configuring adaptive user interface may be provided as described herein. For example, apparatus described in the present disclosure may comprise all or a portion of computing device 1200 and be capable of performing all or a portion of application 1222 such that implementations of indication of a location of an emergency apparatus may be provided as described herein. This described basic configuration is illustrated in FIG. 12 by those components within dashed line 1201.

Computing device 1200 may have additional features or functionality, and additional interfaces to facilitate communications between the basic configurations 1201 and any required devices and interfaces. For example, a bus/interface controller 1240 may be used to facilitate communications between the basic configuration 1201 and one or more data storage devices 1250 via a storage interface bus 1241. The data storage devices 1250 may be removable storage devices 1251, non-removable storage devices 1252, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 1220, removable storage 1251 and non-removable storage 1252 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 1200. Any such computer storage media may be part of device 1200.

Computing device 1200 may also include an interface bus 1242 for facilitating communication from various interface devices (e.g., output interfaces, peripheral interfaces, and communication interfaces) to the basic configuration 1201 via the bus/interface controller 1240. Example output interfaces 1260 may include a graphics processing unit 1261 and an audio processing unit 1262, which may be configured to communicate to various external devices such as a display or speakers via one or more A/V ports 1263. Example peripheral interfaces 1260 may include a serial interface controller 1271 or a parallel interface controller 1272, which may be configured to communicate with external devices such as input devices (e.g., keyboard, mouse, pen, voice input device, touch input device, etc.) or other peripheral devices (e.g., printer, scanner, etc.) via one or more I/O ports 1273. An example communication interface 1280 includes a network controller 1281, which may be arranged to facilitate communications with one or more other computing devices 1290 over a network communication via one or more communication ports 1282. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 1200 may be implemented as a portion of a small-form factor portable (or mobile) electronic device such as a cell phone, a personal data assistant (PDA), a tablet type device, a personal media player device, a wireless web-watch device, a personal headset device, an application specific device, or a hybrid device that includes any of the above functions. Computing device 1200 may also be implemented as a personal computer including both laptop computer and non-laptop computer configurations. In addition, computing device 1200 may be implemented as part of a wireless base station or other wireless system or device.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussion utilizing terms such as "processing," "computing," "calculating," "determining" or the like refer to actions or processes of a computing device that manipulates or transforms data represented as physical electronic or magnetic quantities within memories, registers, or other information storage devices, transmission devices, or display devices of the computing device.

Claimed subject matter is not limited in scope to the particular implementations described herein. For example, some implementations may be in hardware, such as those employed to operate on a device or combination of devices, for example, whereas other implementations may be in software and/or firmware. Likewise, although claimed subject matter is not limited in scope in this respect, some implementations may include one or more articles, such as a signal bearing medium, a storage medium and/or storage media. This storage media, such as CD-ROMs, computer disks, flash memory, or the like, for example, may have instructions stored thereon that, when executed by a computing device such as a computing system, computing platform, or other system, for example, may result in execution of a processor in accordance with claimed subject matter, such as one of the implementations previously described, for example. As one possibility, a computing device may include one or more processing units or processors, one or more input/output devices, such as a display, a keyboard and/or a mouse, and one or more memories, such as static random access memory, dynamic random access memory, flash memory, and/or a hard drive.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skilled in the art in light of this disclosure. In addition, those skilled in the art will appreciate that the mechanisms of the subject matter described herein are capable of being distributed as a product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed:

1. A method of facilitating indication of an automated external defibrillator (AED) that is part of a network of AEDs, the method comprising:
    receiving by the AED, via an electronic communication medium, an indication of a need for the AED, the indication generated in response to an event for which the AED is needed and the indication including information regarding a location of the need;
    determining, by the AED, if the location of the need is within a predetermined radius relative to a location of the AED, the predetermined radius stored at the AED and the determining based, at least in part, on the information regarding the location of the need; and
    when it is determined that the location of the need is within the predetermined radius, activating an electronic indicator device by the AED to facilitate indication of the AED being within the predetermined radius.

2. The method of claim 1 further comprising activating a user interface communicatively coupled to the AED.

3. The method of claim 1, wherein receiving comprises receiving the indication from an emergency service system.

4. The method of claim 1, wherein determining comprises determining if the location of the need is within about 200 meters radius relative to the location of the AED.

5. The method of claim 1, wherein activating comprises activating at least one of a visual indicator and/or an audio indicator.

6. A method of facilitating indication of an automated external defibrillator (AED) of a plurality of AEDs, the method comprising:
    receiving by the AED, via an electronic communication medium, an indication of a need for the AED, the indication generated in response to an event for which the AED is needed and the indication including information regarding a location of the need;
    determining, by the AED, if the location of the need is within a predetermined radius relative to a location of the AED, the predetermined radius stored at the AED and the determining based, at least in part, on the information regarding the location of the need;
    determining if the AED is operationally ready for use; and
    when it is determined that the location of the need is within the predetermined radius and that the AED is operationally ready for use, activating an electronic indicator device of the AED to facilitate indication of the AED being within the predetermined radius and being operationally ready for use.

7. The method of claim 6 further comprising activating a user interface communicatively coupled to the AED.

8. The method of claim 6, wherein receiving comprises receiving the indication from an emergency service system.

9. The method of claim 6, wherein determining if the location of the need is within a predetermined radius comprises determining if the location of the need is within about 200 meters radius relative to the location of the AED.

10. The method of claim 6, wherein activating comprises activating at least one of a visual indicator and/or an audio indicator.

11. A method of facilitating indication of an automated external defibrillator (AED) that is part of a network of AEDs, the method comprising:
    receiving by the AED of the network of AEDs, via an electronic communication medium, an indication of a need for the AED, the indication generated in response to an event for which the AED is needed and the indication including information regarding a location of the need;
    determining, by the AED, if the location of the need is within a predetermined radius relative to a location of AED, the predetermined radius stored at the AED and the determining based, at least in part, on the information regarding the location of the need;
    determining if motion is detected proximate to the AED; and
    when it is determined that the location of the need is within the predetermined radius and that motion is detected, activating an electronic indicator device by the AED to facilitate indication of the AED being within the predetermined radius and that motion is detected.

12. The method of claim 11 further comprising activating a user interface communicatively coupled to the AED.

13. The method of claim 11, wherein receiving comprises receiving the indication from an emergency service system.

14. The method of claim 11, wherein determining if the location of the need is within a predetermined radius comprises determining if the location of the need is within about 200 meter radius relative to the location of the AED.

15. The method of claim 11, wherein activating comprises activating at least one of a visual indictor and/or an audio indicator.

16. A system for facilitating indication of an automated external defibrillator (AED) comprising:
    a transmit and/or receive module (TX/RX);
    a processor communicatively coupled to the TX/RX; and
    an indication alert module (IAM) communicatively coupled to the processor, the IAM configured to:
    receive by the AED, via an electronic communication medium, an indication of a need for the AED, the indication generated in response to an event for which the AED is needed and the indication including information regarding a location of the need;
    determine, by the AED, if the location of the need is within a predetermined radius relative to a location of the AED, the predetermined radius stored at the AED and the determination based, at least in part, on the information regarding the location of the need; and when it is determined that the location of the need is within the predetermined radius, activate an electronic indicator device by the AED to facilitate indication of the AED being within the predetermined radius.

17. The system of claim 16 further comprising an unmanned aerial vehicle (UAV), the UAV configured to facilitate transportation of the AED to location of the need.

* * * * *